United States Patent [19]

Afonso et al.

[11] Patent Number: 5,175,151
[45] Date of Patent: Dec. 29, 1992

[54] ANTIVIRAL COMPOUNDS AND ANTIHYPERTENSIVE COMPOUNDS

[75] Inventors: Adriano Afonso, West Caldwell; Jay Weinstein, Upper Montclair; Margaret J. Gentles, Bloomfield, all of N.J.

[73] Assignee: Schering Corporation, Kenilworth, N.J.

[21] Appl. No.: 830,958

[22] Filed: Feb. 5, 1992

Related U.S. Application Data

[63] Continuation of Ser. No. 579,913, Sep. 7, 1990, abandoned.

[51] Int. Cl.⁵ .......................................... C07D 215/56
[52] U.S. Cl. .................................... 514/63; 514/312; 514/82; 514/432; 514/456; 514/682; 546/14; 546/155; 546/23; 546/153; 544/128; 544/198; 544/238; 544/405; 549/214; 549/283; 549/23; 548/311.4; 548/345.1
[58] Field of Search ............... 514/312, 63; 546/14, 546/155

[56] References Cited

U.S. PATENT DOCUMENTS

| | | | |
|---|---|---|---|
| 3,574,216 | 8/1971 | Bell | 546/155 |
| 3,962,445 | 6/1976 | Buckle et al. | 514/312 |
| 4,006,237 | 1/1977 | Buckle et al. | 514/312 |
| 4,107,310 | 8/1978 | Allais et al. | 514/312 |
| 4,902,693 | 2/1990 | Blythin et al. | 514/312 |
| 4,959,363 | 9/1990 | Wentland | 546/155 |

FOREIGN PATENT DOCUMENTS 0152966  6/1990  Japan ....................... 546/155

OTHER PUBLICATIONS

Yoshizaki et al. Chem Abstr vol. 113 entry 211864z (1990).
Beak et al. Chem. Abstr vol. 78 entry 71111h (1972).
Ishii et al. Chem. Abstr vol. 97 entry 159498t (1982).
Kim et al Chem. Abstr. vol. 96 entry 104124s (1981).
Derwent Abstract J90005-752-B.
Derwent Abstract J89035-827-B.

*Primary Examiner*—Donald G. Daus
*Attorney, Agent, or Firm*—Eric S. Dicker; Henry C. Jeanette; Matthew Boxer

[57] ABSTRACT

Compounds useful as antihypertensive agents, or antiviral agents against DNA containing viruses, such as herpes group viruses, are disclosed. The compounds are represented by Formula 1.0:

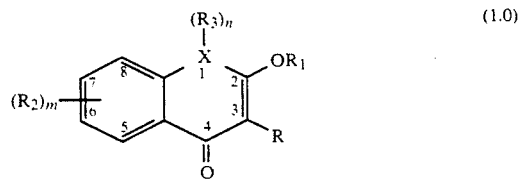

and their pharmaceutically acceptable salts and solvates.

Pharmaceutical compositions containing compounds represented by Formula 1.0 are disclosed. Also disclosed are methods of treating hypertension or a viral infection using compounds represented by Formulas 1.0.

Also disclosed is a compound of Structure B

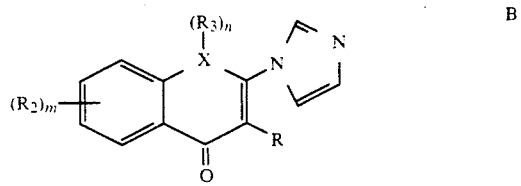

useful as an intermediate in producing compounds of Formula 1.0.

A process for preparing the compounds of Formula 1.0 is also disclosed. In the process a compound of Structure B

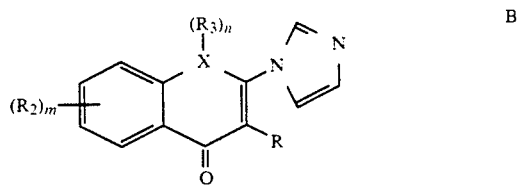

is reacted with an alkoxide $R_1O^-M^+$ in a solvent comprising the corresponding alcohol $R_1OH$ of the alkoxide. Optionally, an organic cosolvent may be used with the solvent.

8 Claims, No Drawings

ANTIVIRAL COMPOUNDS AND ANTIHYPERTENSIVE COMPOUNDS

This is a continuation of application Ser. No. 07/579,913 filed Sep. 7, 1990, abandoned.

BACKGROUND

This invention relates to compounds having antiviral activity and to compounds having antihypertensive activity, pharmaceutical compositions thereof, and methods of treatment utilizing the compositions. In particular, this invention is related to compounds having antiviral activity against herpes group viruses, pharmaceutical compositions containing the compounds, and methods of treating herpes group viruses using the pharmaceutical compositions.

There are four separate herpes group viruses which infect and causes disease in humans. These are (1) herpes simplex virus 1 and 2 (HSV-1 and HSV-2, respectively); (2) cytomegalovirus (CMV); (3) varicellazoster virus (VZ); and (4) Epstein-Barr virus(EB). Examples of diseases associated with herpes simplex virus infection include herpes labialis, genital herpes (herpes progenitalis), neonatal herpes, herpetic keratitis, eczema herpecticum, disseminated herpes, occupational herpes, herpectic gingivostomatitis, meningitis (aseptic), and ecephalitis.

VZ virus is associated with chicken-pox (varicella) and shingles (zoster) in humans.

CMV is wide spread in humans and numerous other mammals. A great majority of humans CMV infections are subclinical; that is, the primary infection occurs with no signs or symptoms. An exception to this is a congenital infection which occasionally gives rise to cytomegalic inclusion body disease in infants. There is also a mononucleosis-like syndrome caused by the virus.

A great majority of serious cases due to CMV infection come from recurring infections in immuno-compromised individuals, such as in transplant patients and in cancer patients. It has been estimated that silent CMV infections have occurred in a majority of humans by the time adulthood is reached.

Examples of drugs used to treat herpes infections include: (1) IUDR (5'-iodo-2'-deoxyuridine); (2) Ara-C (1-[beta-D-arabinofuranosyl]cytosine); (3) Ara-A (9-beta-D-arabinofuranosyladenine); and (4) Acyclovir (9-[(2-hydroxy)methyl]guanine). Also Haines et al. (U.S. Pat. No. 4,757,088 issued Jul. 12, 1988) discloses that lidocaine (2-(diethylamino)-N-(2,6-dimethylphenyl)acetamide) is an antiviral agent in cell culture against HSV-1 and HSV-2, and is able to treat herpes virus infections of mammals. Haines et al. also disclose that lidocaine is particularly effective in the treatment of HSV oral and genital lesions in humans. According to Haines et al., the addition of pantothenic acid or its alcohol and salt forms, dexpanthenol and pantothenate respectively, to lidocaine or lidocaine hydrochloride significantly enhances the antiviral activity of those drugs.

In view of current interest in the art for finding useful antihypertensive and useful antiviral agents, in particular, useful agents against herpes group viruses, any new compounds exhibiting antiviral activity would be a welcome contribution to the art. This invention provides such a contribution.

SUMMARY OF THE INVENTION

This invention provides compounds which are useful as antiviral agents against DNA containing viruses such as herpes group viruses. In particular, the compounds of this invention are useful against HSV-1 and HSV-2 and may also prove useful against CMV and EB.

The compounds of this invention are advantageous over known compounds because they inhibit early events in the viral replication.

One embodiment of this invention provides antiviral compounds of Formula 1.0:

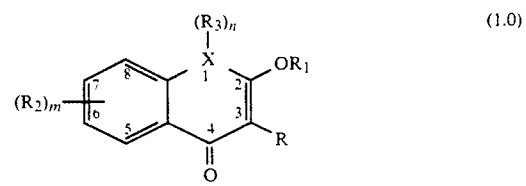

wherein:
(A) X is selected from the group consisting of: N, O, S, and C;
(B) m is an integer from 0 to 4;
(C) R is selected from the group consisting of:
  (1) —C(O)R$_4$ wherein R$_4$ is selected from the group consisting of:
    (a) H;
    (b) alkyl;
    (c) aryl;
    (d) alkaryl;
    (e) alkenyl;
    (f) —N(R$_5$)$_2$ wherein each R$_5$ is independently selected from the group consisting of: H, alkyl, aryl, alkaryl, alkenyl, heteroalkyl, heteroaryl and alkoxy;
    (g) heteroalkyl;
    (h) heteroaryl;
    (i) substituted alkyl;
    (j) alkoxy; and
    (k) —NHC(O)R$_6$ wherein R$_6$ is selected from the group consisting of: alkyl, aryl, alkaryl, heteroalkyl, heteroaryl, and H;
  (2)

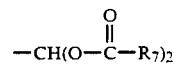

wherein R$_7$ is selected from the group consisting of alkyl, aryl, alkaryl, alkenyl, heteroalkyl, and heteroaryl;
  (3)

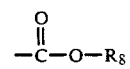

wherein R$_8$ is selected from the group consisting of aryl, alkanyl, heteroalkyl, heteroaryl, and H;
  (4) alkyl;
  (5)

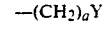

wherein a is an integer from 1 to 6 and Y is a halogen atom selected from the group consisting of Cl, F, Br and I;

(6)

—(CH$_2$)$_b$R$_9$ wherein b is an integer of 1 to 6 and R$_9$ is a heteroaryl;

(7) alkenyl;

(8)

$$-\overset{(O)_c}{\underset{|}{S}}-R_7$$

wherein c is an integer from 1 to 2 and R$_7$ is as defined above;

(9)

—SR$_{10}$ wherein R$_{10}$ is selected from the group consisting of alkyl, aryl, alkaryl, alkenyl, heteroalkyl, heteroaryl, heterocycles, and

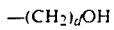
—(CH$_2$)$_d$OH wherein d is an integer from 1 to 6;

(10) heterocyclyl;

(11)

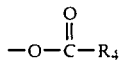
$$-O-\overset{O}{\underset{\|}{C}}-R_4$$

wherein R$_4$ is as defined above;

(12)

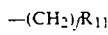
—(CH$_2$)$_f$R$_{11}$ wherein f is an integer of 1 to 10, and R$_{11}$ is selected from the group consisting of: aryl, alkenyl, —OR$_7$, —OH, —NO$_2$, —NHR$_7$, N(R$_7$)$_2$, and —C(O)R$_4$, wherein each R$_7$ is the same or different, and wherein R$_4$ and R$_7$ are as above defined;

(13) aryl;

(14)

—CH(OR$_6$)$_2$ wherein R$_6$ is as above defined;

(15)

—CH=NOR$_{12}$ wherein R$_{12}$ is selected from the group consisting of: H, alkyl, and

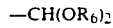
—(CH$_2$)$_g$R$_{13}$ wherein g is an integer from 1 to 2 and R$_{13}$ is selected from the group consisting of: C(O)OH, phenyl, heteroaryl, —NHR$_7$, —N(R$_7$)$_2$, —SO$_3$H, and —SO$_2$NH$_2$, wherein R$_7$ is as above defined;

(16)

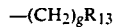
—CH=N(CH$_2$)$_h$R$_{14}$ wherein h is an integer from 1 to 10, and R$_{14}$ is selected from the group consisting of: —OH, —NHR$_7$, —N(R$_7$)$_2$, —C(O)R$_4$ wherein R$_4$ is alkoxy, —C(O)OR$_8$, aryl, and heteroaryl, wherein R$_4$, R$_7$ and R$_8$ are as above defined;

(17) H;

(18) —S$^+$(R$_{15}$)$_2$ wherein each R$_{15}$ is the same or different alkyl group;

(19) —NO$_2$;

(20) —NO;

(21) —NH$_2$;

(22) —NHR$_7$ wherein R$_7$ is as above defined;

(23) —N(R$_7$)$_2$ wherein R$_7$ is as above defined;

(24) —NHC(O)R$_6$ wherein R$_6$ is as above defined; and

(25) halogen atoms selected from the group consisting of: F, Cl, Br, and I;

(D) R$_1$ is selected from the group consisting of:
(1) alkyl;
(2) alkenyl halide having from 1 to about 2 double bonds wherein the halogen atoms are selected from the group consisting of: F, Cl, Br, and I;
(3) —(CH$_2$)$_i$N(R$_{16}$)(R$_{17}$) wherein i is an integer from 1 to 6, R$_{16}$ and R$_{17}$ are the same or different and are selected from the group consisting of: H and alkyl;
(4) acyl having the formula —C(O)R$_4$ wherein R$_4$ is as above defined; and
(5) —(CH$_2$)$_a$C(H)$_{3-e}$Z$_e$ wherein a is as above defined; e is an integer from 1 to 3 and when e is 2 or 3, each Z is the same or different; and Z is selected from the group consisting of: —C(O)O—alkyl, —C(O)OH, —OH and —O—alkyl;

(E) Each R$_2$ for each m is independently selected from the group consisting of:
(1) alkyl;
(2) alkoxy;
(3) aryloxy;
(4) aryl;
(5) aralkyloxy;
(6) halogen atoms selected from the group consisting of: F, Cl, Br and I;
(7)

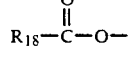
$$R_{18}-\overset{O}{\underset{\|}{C}}-O-$$

wherein R$_{18}$ is selected from the group consisting of: alkyl, alkaryl, alkenyl, heteroalkyl, and heteroaryl;

(8)

—N(R$_{19}$)$_2$ wherein each R$_{19}$ is independently selected from the group consisting of: H, alkyl, aryl, and R$_{20}$C(O)— wherein R$_{20}$ is selected from the group consisting of: alkyl, aryl, alkaryl, alkenyl, heteroalkyl, and heteroaryl;

(9)

—OH;

(10)

—CH$_2$OH;

(11)

(12)

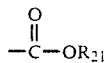

wherein $R_{21}$ is selected from the group consisting of: alkyl and aryl;

(13)

(14)

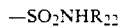

wherein $R_{22}$ is selected from the group consisting of: alkyl, aryl and H;

(15)

(16)

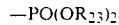

wherein $R_{23}$ is selected from the group consisting of: alkyl and aryl;

(17) —$OPO_3H$;
(18) —$OP(OR_{23})_2$ wherein $R_{23}$ is as above defined; and
(19) —$CF_3$;

(F) n is:
  (1) 1 when X is N;
  (2) 0 when X is S;
  (3) 0 when X is O; and
  (4) 2 when X is C, and each $R_3$ is the same or different;

(G) is selected from the group consisting of:
  (1) alkyl;
  (2) aralkyl;
  (3) aryl;
  (4) substituted aryl;
  (5) alkaryl;
  (6) alkyl heteroaryl;
  (7) alkyloxyalkyloxyaryl;
  (8) —$(CH_2)_j R_{24}$ wherein j is an integer from 1 to 6 and $R_{24}$ is selected from the group consisting of:
    (a) —$C(O)OR_{25}$ wherein $R_{25}$ is selected from the group consisting of: alkyl, alkenyl, and H;
    (b) —$N(R_{25})_2$ wherein each $R_{25}$ is the same or different, and $R_{25}$ is as defined above;
    (c) —$R_{25}$ wherein $R_{25}$ is as defined above; and
    (d) —$OR_{25}$ wherein $R_{25}$ is as defined above;
  (9) H; and
  (10) —$OR_{26}$ wherein $R_{26}$ is selected from the group consisting of H, alkyl, alkaryl, alkenyl, heteroalkyl, and heteroaryl.

Another embodiment of this invention provides antihypertensive compounds of Formula 1.0 wherein:
(A) R is selected from the group consisting of: H and —$C(O)OR_6$ wherein $R_6$ is as defined above;
(B) $R_1$ is alkyl; and
(C) $R_2$, m, $R_3$ and n are as above defined.

Preferably R is selected from the group consisting of: H and —$C(O)OR_6$ wherein $R_6$ is alkyl with ethyl being preferred. Preferably $R_1$ is methyl. Preferably $R_2$ is an alkyl group with methyl being preferred or an alkoxy group with methoxy being preferred. Preferably $R_3$ is alkyl or aralkyl, with methyl, hexyl, heptyl or benzyl being preferred.

Another embodiment of this invention provides pharmaceutical compositions comprising an effective amount of a pharmaceutically acceptable carrier and an effective amount of an antiviral or an antihypertensive compound of this invention. Preferably the compounds having antihypertensive activity are selected from the group consisting of compound numbers 3,4,5,10,15,16 and 17 of Table I. Preferably the compounds having antiviral activity are selected from the group consisting of compound numbers 1–17 of Table I with 3–13 being most preferred and 5,6,7,8,9, and 11 being even more preferred.

In yet another embodiment this invention provides a method of treating a patient suffering from hypertension or having a viral infection by administering to such a patient an effective amount of an antihypertensive or an antiviral compound of this invention. Generally, in the method of treatment the compound is administered as one of the pharmaceutical compositions of this invention. Examples of viral infections treatable in accordance with the methods of this invention include the DNA containing viruses such as the herpes viruses discussed above (e.g., HSV-1, HSV-2, CMV, VZ, EB, and the like).

A further embodiment of this invention provides a compound of Structure B:

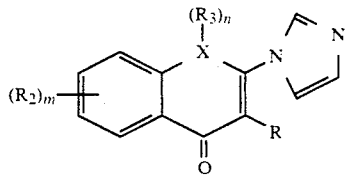

B wherein R, m, $R_2$, n, and $R_3$ are as defined above. Preferably R is H.

In still another embodiment this invention provides a process for preparing compounds of Formula 1.0. In this process compounds of Structure B are reacted with an alkoxide $R_1O^-M^+$ in a solvent comprising the corresponding alcohol $R_1OH$ of said alkoxide. Optionally, an organic co-solvent may be used with the solvent.

DETAILED DESCRIPTION OF THE INVENTION

When used herein, the terms listed below have the scope indicated, unless indicated otherwise.

Alkaryl—represents an aryl group, as defined below, in which an alkyl group, as defined below, is substituted for one of the aryl H atoms. The aryl group may contain additional substituents selected from the group consisting of: halogen atoms (e.g., Cl, Br, F, and/or I), alkoxy, alkyl, and amino. Representative examples include $CH_3$phenyl-, $CH_3CH_2$phenyl- and the like.

Alkenyl (alkylene)—represents straight and branched carbon chains having at least one carbon to carbon double bond and preferably having from 2 to 6 carbon atoms. Preferably the alkenyl substituent has from 1 to 2 double bonds. Representative examples include vinyl, allyl, butenyl and the like.

Alkoxy—represents an alkyl radical attached to a molecule through an oxygen atom (—O-alkyl). Representative examples include methoxy, ethoxy and the like.

Alkyl—represents straight or branched carbon chains, which contain from 1 to 6 carbon atoms. Representative examples include methyl, ethyl, propyl and the like.

Alkyl heteroaryl(alkheteroaryl)—represents a heteroaryl group as defined below, wherein an alkyl group, as defined above, is substituted for one of the aryl H atoms. Representative examples include pyridylmethyl, furylmethyl and the like.

Alkyloxyalkyloxyaryl—represents a group wherein an alkyl group is joined through an oxygen atom to another alkyl group which in turn is joined through an oxygen atom to an aryl group wherein the point of attachment to the aryl group is at a ring carbon. Alkyl is as defined above and aryl is as defined below. The aryl group may contain additional substituents selected from the group consisting of: halogen atoms (e.g., Cl, Br, F, and/or I), alkoxy, alkyl, and amino. Representative examples include phenoxypropyloxymethyl, phenoxyethoxymethyl and the like.

Aralkyl—represents an alkyl group as defined above in which an aryl group as defined below is substituted for one of the alkyl hydrogen atoms. Representative examples include —CH₂phenyl, —CH₂CH₂phenyl, p-hydroxybenzyl, p-(t-butyldimethylsilyoxy)benzyl and the like.

Aralkyloxy—represents an aralkyl group as defined above, which is attached to a molecule by an oxygen atom (aralkyl—O—). The aryl group may contain additional substituents selected from the group consisting of: halogen atoms (e.g., Cl, Br, F, and/or I), alkoxy, alkyl, and amino. Representative examples include benzyloxy, phenethoxy, and the like.

Aryl—represents a mono- or bi-cyclic aromatic system. Examples of preferred aryl groups include those having from 6 to 14 carbon atoms. Representative examples include phenyl, 1-naphthyl, 2-naphthyl and indanyl. The aryl group may contain additional substituents selected from the group consisting of: halogen atoms (e.g., Cl, Br, F, and/or I), alkoxy, alkyl, and amino.

Aryloxy—represents an aryl group as defined above, which is attached through an oxygen atom (aryl—O—). The aryl may contain additional substituents selected from the group consisting of: halogen atoms, (e.g., Cl, Br, F, and/or I), alkoxy, alkyl, and amino. Representative examples include phenoxy, naphthyloxy, and the like.

Heteroalkyl—represents an alkyl group, as defined above, wherein one or more heteroatoms are substituted for one or more of the alkyl H atoms. The heteroatoms are independently selected from the group consisting of: O, S, and N. Representative examples of heteroalkyl groups include hydroxyethyl, aminoethyl, mercaptoethyl, and the like.

Heteroaryl (including the heteroaryl portion of heteroarylmethyl)—represents aromatic systems having at least one O, S and/or N heteroatom in the ring structure. Examples of preferred heteroaryl groups include those containing from 3 to 14 carbon atoms. Representative examples of heteroaryl groups include but are not limited to: 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-, 4- or 5-pyrazolyl, 2-, 4- or 5-oxazolyl, 2- or 3-pyrrolyl, 2- or 3-N-methylpyrrolyl, and the like.

Heterocyclic (heterocycles, heterocyclyl)—represents non-aromatic cyclic groups having at least one O, S, and/or N heteroatom interrupting a carbocyclic ring structure containing from about 3 to about 6 carbon atoms. Preferably the heterocyclic groups contain about 3 to about 4 carbon atoms. Examples of heterocyclic groups include but are not limited to thiazoline (thiazolinyl), thiazolidone (thiazolidinyl), dioxolane (dioxolanyl), morpholine (morpholinyl) and the like.

Substituted alkyl—represents an alkyl group, as defined above, wherein one or more of the alkyl H atoms are replaced with groups selected from the group consisting of: alkyl, aryl, heteroaryl —OH, —O—alkyl, —NH₂, —N(alkyl)₂ wherein each alkyl group is the same or different, —S—alkyl, —C(O)O—alkyl, —C(O)H, —NHC(NH)NH₂ (wherein the C(NH) portion represents C=NH), —C(O)NH₂, —OC(O)NH₂, NO₂ and —NHC(O)-alkyl, wherein alkyl, aryl, and heteroaryl are as above defined.

Substituted aryl—represents an aryl group, as defined above, wherein one of more of the H atoms attached to the ring carbon atoms are replaced by groups independently selected from the group consisting of: halo, alkyl, hydroxy, alkoxy, phenoxy, amino, alkylamino, and dialkylamino. Preferred substituted aryl groups are substituted phenyl groups.

Also, as used herein, unless stated otherwise, C(O) represents C=O and Ar represents aromatic.

Representative examples of R₂ include:

  (1)

  (2)

  (3)

  (4)

  (5)

  (6)

  (7)

Representative examples of R₃ include:

  (1)

  (2)

  (3)

  (4)

-continued

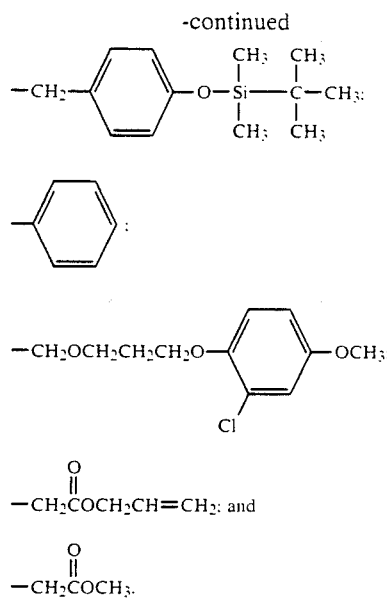

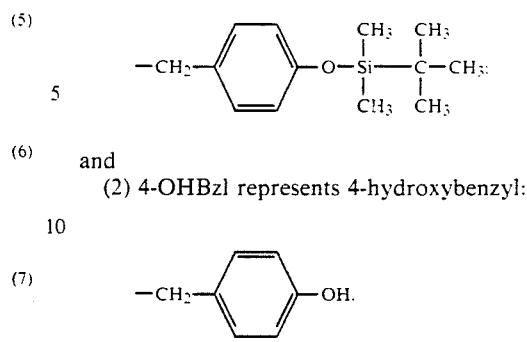

and (2) 4-OHBzl represents 4-hydroxybenzyl:

Certain compounds of this invention may exist in isomeric forms. The invention contemplates all such isomers both in pure form and in admixture, including racemic mixtures.

Certain compounds of the invention can exist in unsolvated as well as solvated forms, including hydrated forms, e.g., hemihydrate. In general, the solvated forms, with pharmaceutically acceptable solvents such as water, ethanol and the like are equivalent to the unsolvated forms for purposes of the invention.

Certain compounds of the invention will be acidic in nature, e.g., those compounds which possess a carboxyl or phenolic hydroxyl group. These compounds may form pharmaceutically acceptable salts. Examples of such salts are the sodium, potassium, calcium, and aluminum salts. Also contemplated are salts formed with pharmaceutically acceptable amines such as ammonia, alkylamines, hydroxyalkylamines, N-methylglucamine and the like.

Certain compounds of the invention, e.g., those with a basic amine group, also form pharmaceutically acceptable salts with organic and inorganic acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous Preferably R is selected from the group consisting of: H; —C(O)R$_4$ wherein R$_4$ is alkoxy with ethoxy being preferred; and halogen (such as Cl, F, Br or I) with Cl or I being preferred. Preferably R$_1$ is alkyl with methyl being preferred. Preferably R$_2$ is alkyl or alkoxy with methyl or methoxy, respectively, being preferred, with m being preferably 1 or 2. Preferably R$_3$ is alkyl or aralkyl. Most preferably R$_3$ is hexyl, heptyl, benzyl, 4-hydroxybenzyl or 4-t-butyldimethylsilyloxybenzyl. Preferably X is nitrogen and therefore n is preferably 1.

Compounds of this invention include compounds of Formula 1.0 which are selected from the group consisting of compounds represented by compound numbers 1 to 17 which are set forth in Table I:

TABLE I

| No. | X | R | R$_1$ | R$_2$ | R$_3$ |
|---|---|---|---|---|---|
| 1 | N | H | —(CH$_2$)$_2$N(CH$_3$)$_2$ | — | —CH$_3$ |
| 2 | N | H | —C$_2$H$_5$ | — | —CH$_3$ |
| 3 | N | H | —CH$_3$ | 6-CH$_3$ | Bzl |
| 4 | N | H | —CH$_3$ | — | Bzl |
| 5 | N | H | —CH$_3$ | — | —C$_7$H$_{15}$ |
| 6 | N | H | —CH$_3$ | 8-CH$_3$ | —C$_6$H$_{13}$ |
| 7 | N | H | —CH$_3$ | 8-OCH$_3$ | —C$_6$H$_{13}$ |
| 8 | N | H | —CH$_3$ | 6-CH$_3$ 7-CH$_3$ | SiOBzl |
| 9 | N | —C(O)OCH$_2$H$_5$ | —CH$_3$ | 6-CH$_3$ | Bzl |
| 10 | O | H | —CH$_3$ | 7-OCH$_3$ 8-CH$_3$ | — |
| 11 | N | H | —CH$_3$ | 6-CH$_3$ 7-CH$_3$ | 4-OHBzl |
| 12 | N | Cl | —CH$_3$ | 6-CH$_3$ | Bzl |
| 13 | N | I | —CH$_3$ | — | Bzl |
| 14 | N | H | —(CH$_2$)$_2$OH | — | —CH$_3$ |
| 15 | N | H | —CH$_3$ | 8-CH$_3$ | —CH$_3$ |
| 16 and | N | H | —CH$_3$ | 6-CH$_3$ | —C$_6$H$_{13}$ |
| 17 | N | —C(O)OC$_2$H$_5$ | —CH$_3$ | — | —C$_6$H$_{13}$ | wherein:
(1) SiOBzl represents 4-t-butyldimethylsilyloxybenzyl:

base solution such as dilute aqueous sodium hydroxide, potassium carbonate, ammonia and sodium bicarbonate. The free base forms differ from their respective salt forms somewhat in certain physical properties, such as solubility in polar solvents, but the salts are otherwise equivalent to their respective free base forms for purposes of this invention.

The compounds of Formula 1.0 can be prepared by the processes described below. In these processes the substituents are as described above, unless indicated otherwise. Those skilled in the art will appreciate that in the processes described below the reactions are carried out at a temperature high enough to allow the reaction to proceed at a reasonable rate, but not so high as to cause undue degradation of reactants and/or products. Those skilled in the art will also appreciate that in the following reactions the desired products may be isolated by techiques well known in the art such as distillation, column chromatography, recrystallization, and the like.

Compounds of Formula 1.0 wherein $R_1$, $R_2$, and $R_3$ are as defined above, and R is H, alkyl, alkenyl, aryl, $C(O)R_4$, $S^+(R_{15})_2$, $SR_{10}$, $S(O)_cR_7$, $NO_2$, NO, $NH_2$, $NHR_7$, $N(R_7)_2$, $NHC(O)R_6$ or halogen, are prepared by reacting compounds of Structure A

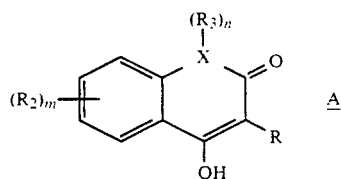

with a diazoalkane or alkyl halide or substituted alkyl halide or acyl halide using reaction conditions known in the art (see, for example, J. March, *Advanced Organic Chemistry*, John Wiley & Sons, Publishers, 1985, sections 0.14, 0.17, and 0.22, the disclosures of which are incorporated herein by reference thereto). In the process, compounds of Formula 1.0 are formed as minor products, the isomeric enol ether being formed as the major product.

Compounds of Formula 1.0 wherein $R_1$, $R_2$, and $R_3$ are as defined above for Formula 1.0, and R is —CH-$(OC(O)R_7)_2$, —CH$(OR_6)_2$, —CH=N$(CH_2)_hR_{14}$, —CH=NOR$_{12}$, heterocyclyl, —$(CH_2)_aY$, —$(CH_2)_bR_9$, or —$(CH_2)_fR_{11}$ are prepared from compounds of Formula 1.0 wherein $R_1$, $R_2$ and $R_3$ are as defined above and R is —C(O)O-alkyl, using reactions known in the art for esters, aldehydes and alkyl halides (see, for example, J. March, cited above, pages 1289, 1291 and 1301, the disclosures of which are incorporated herein by reference thereto).

A preferred process for preparing compounds of Formula 1.0 comprises reacting compounds of Structure B.

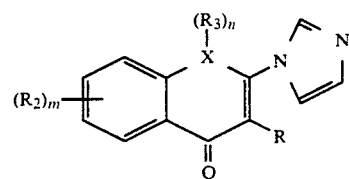

wherein, R, $R_1$, $R_2$, m, $R_3$ and n are as defined above (and wherein R is preferably H), with an alkoxide $R_1O^-M^-$ in a solvent consisting of the corresponding alcohol $R_1OH$ (wherein $R_1$ is as defined above) with or without an organic co-solvent capable of dissolving and mixing with the alcohol $R_1OH$ and the compound of Structure B. The amount of $R_1O^-M^-$ used may be from about 0.1 to about 2.0 equivalents based on the weight of Structure B (vol/wt), preferably about 0.1 to about 1.0 equivalents and most preferably about 0.25 equivalents. The cation ($M^+$) of the alkoxide may be selected from the group consisting of: $Na^+$, $K^+$, $Li^+$, $Mg^{++}$ and $Ca^{++}$. Preferably $Na^+$, $K^+$ or $Li^+$ is used, and most preferably $Na^+$ is used.

The reaction solvent is the alcohol $R_1OH$ itself or a co-solvent may be used with the alcohol. Examples of co-solvents include but are not limited to: tetrahydrofuran, dichloromethane, dimethylformamide and the like. Preferably the solvent is an equivalent amount of $R_1OH$ to Structure B (vol/wt) together with 10 times the volume of dimethylformamide. Most preferably, the solvent is $R_1OH$ in an amount which is 10 times the equivalent amount (volume) of Structure B.

The reaction is carried out within a temperature range of about 0° C. to about 100° C., preferably at room temperature (about 22° C.) to about 60° C., and most preferably at room temperature. The reaction is usually complete within 1 to 16 hours.

Compounds of Structure B are prepared by reacting an isatoic anhydride of Structure C

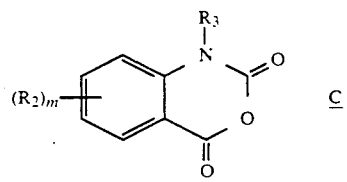

with a phosphorane of Structure D

R—C=P(Ph)₃          D (wherein Ph represents phenyl) followed by acidification to give an intermediate compound of Structure E

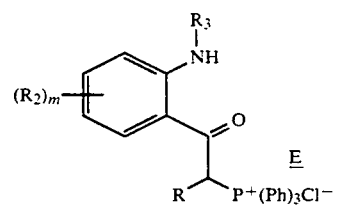

The reaction may be run in organic solvents, such as tetrahydrofuran, methylene chloride and the like, at temperatures ranging from about 0° to about 22° C. and preferably at about 22° C. The reaction is usually complete in about 15 minutes. Mineral acid, such as aqueous hydrochloric or sulfuric acid is used in the acification step.

The compound of Structure E is reacted with thiocarbonyldiimidazole in a basic solvent, such as pyridine, with or without a catalyst, such as dimethylaminopyridine, at about 22° C. for about 1 to about 2 hours. The reaction mixture is then treated with a base, such as aqueous sodium carbonate, to give an intermediate compound of Structure F

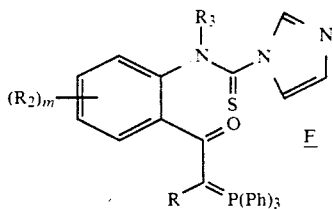

The compound of Structure F is then cyclized in a non-polar organic solvent, such as benzene or toluene, at reflux temperature to give a compound of Structure B.

The compounds of this invention can be administered in any number of conventional dosage forms, e.g., topical, oral, parenteral, rectal, transdermal, inhalation and the like. Oral or rectal dosage forms include capsules, tablets, pills, powders, cachets and suppositories. Liquid oral dosage forms include solutions and suspensions. Parenteral preparations include sterile solutions and suspensions. Inhalation administration can be in the form of a nasal or oral spray, or by insufflation. Topical dosage forms can be creams, ointments, lotions, transdermal devices (e.g., of the conventional patch or matrix type) and the like.

The formulations and pharmaceutical compositions contemplated by the above dosage forms can be prepared with conventional pharmaceutically acceptable excipients and additives, using conventional techniques. Such pharmaceutically acceptable excipients and additives are intended to include carriers, binders, flavorings, buffers, thickeners, color agents, stabilizing agents, emulsifying agents, dispersing agents, suspending agents, perfumes, preservatives lubricants, etc.

Suitable pharmaceutical acceptable solid carriers are magnesium carbonate, magnesium stearate, talc, sugar, lactose, pectin, dextrin, starch, gelatin, tragacanth, methylcellulose, sodium carboxymethylcellulose, low melting waxes, cocoa butter and the like. Capsules can be made wherein the active compound is inserted into pharmaceutically acceptable capsules as a carrier. The active compounds of this invention can be mixed with pharmaceutically acceptable excipients or be used in finely divided powder form without excipients for inclusion into the capsules. Similarly, cachets are included.

Liquid form preparations include solutions, suspensions and emulsions such as water or water-propylene glycol solutions for parenteral injection. Liquid preparations can also be formulated in solution in polyethylene glycol and/or propylene glycol, which may contain water. Aqueous solutions suitable for oral use can be prepared by adding the active component in water and adding suitable colorants, flavors, stabilizing, sweetening, solubilizing the thickening agents as desired. Aqueous suspensions suitable for oral use can be made by dispersing the active component in finely divided form in water with viscous material, i.e., pharmaceutically acceptable natural or synthetic gums, resins, methylcellulose, sodium carboxymethylcellulose and other well-known suspending agents.

Formulations for topical application may include the above liquid forms, as well as creams, aerosols, sprays, dusts, powders, lotions and ointments which are prepared by combining an active ingredient according to this invention with conventional pharmaceutical acceptable diluents and carriers commonly used in topical dry, liquid, cream and aerosol formulations. Ointment and creams may, for example, be formulated with an aqueous or oily base with the addition of suitable thickening and/or gelling agents. Such bases may, thus, for example, include water and/or an oil such as liquid paraffin or a vegetable oil such as peanut oil or castor oil. Thickening agents which may be used according to the nature of the base include soft paraffin, aluminum stearate, cetostearyl alcohol, propylene glycol, polyethylene glycols, woolfat, hydrogenated lanolin, beeswax, etc.

Lotions may be formulations with an aqueous or oil base and will, in general, also include one or more of pharmaceutically acceptable stabilizing agents, emulsifying agents, dispersing agents, suspending agents, thickening agents, coloring agents, perfumes and the like.

Powders may be formed with the aid of any suitable pharmaceutically acceptable powder base, e.g., talc, lactose, starch, etc. Drops may be formulated with an aqueous base or non-aqueous base also comprising one or more pharmaceutically acceptable dispersing agents, suspending agents, solubilizing agents, etc.

The topical pharmaceutical compositions may also include one or more preservatives or bacteriostatic agents, e.g., methyl hydroxybenzoate, propyl hydroxybenzoate, chlorocresol, benzalkonium chlorides, etc.

The topical pharmaceutical compositions may also contain an active compound of this invention in combination with other active ingredients such as antimicrobial agents, particularly antibiotics, anesthetics, analgesics and antipruritic agents.

Also included are solid form preparations which are intended to be converted, shortly before use, to liquid form preparations for either oral or parenteral administration. Such liquid forms include solutions, suspensions and emulsions. These particular solid form preparations are most conveniently provided in unit dose form and as such are used to provide a single liquid dosage unit. Alternatively, sufficient solid may be provided so that after conversion to liquid form, multiple individual liquid doses may be obtained by measuring predetermined volumes of the liquid form preparation as with a syringe, teaspoon or other volumetric container. When multiple liquid doses are so prepared, it is preferred to maintain the unused portion of said liquid doses under conditions which retard possible decomposition. The solid form preparations intended to be converted to liquid form may contain, in addition to the active material, pharmaceutically acceptable flavorants, colorants, stabilizers, buffers, artificial and natural sweeteners, dispersants, thickeners, solubilizing agents and the like. The solvent utilized for preparing the liquid form preparation may be water, isotonic water, ethanol, glycerine, propylene glycol and the like as well as mixtures thereof. Naturally, the solvent utilized will be chosen with regard to the route of administration, for example, liquid preparations containing large amounts of ethanol are not suitable for parenteral use.

The compounds of this invention may also be deliverable transdermally for systemic distribution. The transdermal compositions can take the form of creams, lotions and/or emulsions and can be included in a transdermal patch of the matrix or reservoir type as are conventional in the art for this purpose.

The compounds of this invention may be administered by any conventional mode of administration, by employing an antiviral or antihypertensive effective amount of a compound of this invention for such mode. The dosages may be varied depending upon the requirements of the patient in the judgment of the attending clinician, the severity of the condition being treated and the particular compound being employed. Determination of the proper dosage for a particular situation is within the skill of the art. Treatment can be initiated with smaller dosages which are less than the optimum dose of the compound. Thereafter, the dosage should be increased by small increments until the optimum effect under the circumstances is reached. For convenience, the total daily dosage may be divided and administered in portions during the day if desired.

Thus, depending on the mode, dosages of from about 0.1 to about 100 mg/kg of body weight per day may be administered to provide antihypertensive or antiviral activity. For example, when administered orally doses of from about 20 to about 60 mg/kg of body weight may be used; and when administered parenterally, e.g., intravenously, dosages of from about 5 to about 20 mg/kg body weight may be used.

When administered topically, the amount of compound administered varies widely with the amount of skin being treated, as well as with the concentration of active ingredient applied to the affected area. Preferably, topical compositions contain from about 0.10 to about 10 percent by weight of the active ingredient and are applied as needed according to the judgment of the attending clinician. When administered rectally, the compounds of this invention may be administered in daily doses ranging from about 0.1 mg/kg to about 100 mg/kg.

The dosage to be administered and the route of administration depends upon the particular compound used, the age and general health of the patient and the severity of the viral condition. Thus, the dose ultimately decided upon must be left to the judgment of a trained health-care practitioner.

EXAMPLES

The following examples are illustrative only and should not be construed as limiting the invention in any way. Those skilled in the art will appreciate that variations are possible which are within the spirit and scope of the appended claims.

PREPARATION A

1-Benzyl-4-Hydroxy-6-Methyl-2(1H)-Quinolinone

Step (1): Preparation of 6-methyl-isatoic anhyride.

A solution of 2-amino-5-methyl-benzoic acid (4.5 gm) in 2N HCl (15 ml) and water (35 ml) was stirred vigorously while adding dropwise trichloromethyl chloroformate (5.6 gm). The reaction was stirred for an additional 10 mins and then filtered; the solid cake was washed with water and dried under reduced pressure to give 6-methyl-isatoic anhydride as a light yellow powder (4.7 gm).

Step (2): Preparation of 1-Benzyl-6-Methyl-Isatoic Anhydride.

A solution of 6-methyl-isatoic anhydride (4.5 gm) in DMF (30 ml) was added dropwise to a stirred suspension of 60% sodium hydride (1.0 gm) in DMF (20 ml) under nitrogen atmosphere. The reaction was then warmed to 45° C. and stirred until hydrogen evolution ceased. It was then cooled and a solution of benzyl bromide (4.4 gm) in DMF (10 ml) was added slowly. Stirring was continued for one hour at room temperature and the solution was then evaporated under reduced pressure at 45° C. The resulting solid was suspended in methylene chloride, the insoluble inorganic solid was removed by filtration and the filtrate was evaporated to give 1-benzyl-6-methyl-isatoic anhydride as a crystalline solid.

Step (3): Preparation of 1-Benzyl-3-Carbethoxy-4-Hydroxy-6-Methyl-2(1H)-Quinolinone.

A solution of diethyl malonate (4.07 gm) in dimethyl acetamide (DMA) (10 ml) was added dropwise to a stirred suspension of 60% sodium hydride (1.01 gm) in the same solvent (10 ml), under a nitrogen atmosphere, in an oil bath at 25° C. After hydrogen evolution ceased, the temperature was raised to 80° C. while adding a solution of 1-benzyl-6-methyl-isatoic anhydride (4.5 gm) in DMA (50 ml). After carbon dioxide evolution ceased, the reaction mixture was heated at 120° C. for 17 hours and then was concentrated under reduced pressure to a volume of 25 ml. and then was diluted with water (50 ml). The milky solution was washed with ether, the aqueous layer was acidified with mineral acid to pH3 and the resulting crystalline product 1-benzyl-3-carbethoxy-6-methyl-2(1H)-quinolinone was isolated by filtration.

Step (4): Preparation of 1-Benzyl-4-Hydroxy-6-Methyl-2(1H)-Quinolinone.

The product from Step (3) was dissolved in 2N sodium hydroxide (150 ml) and the solution was refluxed for 4 hrs. Then the solution was cooled and acidified with mineral acid to pH3. The solid was filtered, dried and crystallized from ethyl acetate/hexane to give 1-benzyl-4-hydroxy-6-methyl-2(1H)-quinolinone (4.0 gm). That the expected product was obtained was confirmed by the spectral data: MS: m/e 265 (M•+); NMR (DMSO): δ 2.32 (s, 3H, $CH_3$—Ar), 5.43(s, 2H, $CH_2$—Ar), 5.96(s, 1H, =CH—), 11.48(s, 1H, OH) ppm.

PREPARATION B

1-Benzyl-4-Hydroxy-2(1H)-Quinolinone

Obtained by using isatoic anhydride in Step 2 of Preparation A. That the expected product was obtained was confirmed by the spectral data: MS: m/e 251 (M•+); NMR(DMSO): δ 5.47(s, 2H, $CH_2$—Ar), 6.03(s, 1H, =CH), 11.6(s, 1H, OH) ppm.

PREPARATION C

1-Methyl-2-(1-Imidazolyl)-4-(1H)-Quinolinone

Step (1): Butyl lithium in toluene (2.5M, 2.25 ml) was added dropwise to a suspension of methyltriphenyl phosphonium bromide (2.0 g) in tetrahydrofuran (20 ml). The solution was stirred for 10 minutes followed by the addition of isatoic anhydride (0.5 g) in tetrahydrofuran (10 ml). After 15 minutes, 1N HCl (10 ml) was added dropwise and when carbon dioxide evolution had stopped the mixture was treated with aqueous sodium carbonate until pH 8 was obtained. Then the mixture was extracted with ethyl acetate. The organic extract was dried and evaporated under reduced pressure.

Step (2): The product from Step (1) was dissolved in pyridine (10 ml), the solution was cooled in an ice-bath and treated with carbonyl diimidazole (0.5 g) and dimethylaminopyridine (0.05 g). The reaction was stirred for 1 hour, diluted with ethyl acetate, washed with water, dried and evaporated under reduced pressure.

Step (3): The product from Step (2) was dissolved in toluene (80 ml), refluxed for 24 hours and then evaporated under reduced pressure. The crude product was chromatographed on silica gel to give the title compound which crystallized as white needles (0.14 g) from dichloromethane-ethyl acetate. That the expected product was obtained was confirmed by the spectral data: MS: m/e 225 (M•+); NMR(CDCl$_3$): δ 3.48 (s, 3H, CH$_3$N); 6.30 (s, 1H, CH=), 7.2, 7.32, 7.78 (s, 3H, Im CH=) wherein Im represents imidazole.

EXAMPLE 1

1-Methyl-2-(2-Dimethylaminoethoxy)-4(1H)-Quinolinone (Compound No. 1 of Table I)

Dimethylaminoethanol (0.2 ml) in dimethylformamide (2 ml) was stirred with 60% sodium hydride (10 mg) for 10 minutes followed by the introduction of the product from Preparation C (0.2 g). The mixture was heated at 60° C. for 1 hour and then evaporated under reduced pressure. The crude product was purified by chromatography on silica gel and crystallized from ethyl acetate-hexane as pale yellow crystals. That the expected product was obtained was confirmed by the spectral data: MS: m/e 246 (M•+); NMR(CDCl$_3$): δ 2.35 (s, 6H, N(CH$_3$)$_2$), 2.80 (t, 2H, CH$_2$N), 3.70 (s, 3H, CH$_3$—N), 4.22 (t, 2H, CH$_2$O), 5.88 (s, 1H, CH=).

EXAMPLE 2

1-Methyl-2-Ethoxy-4-(1H)-Quinolinone (Compound No. 2 of Table I)

Ethanol (3 ml) in dichloromethane (5 ml) was stirred with 60% sodium hydride (10 gm) followed by the introduction of the product from Preparation C (0.2 g). The mixture was refluxed for 3 hours, evaporated to dryness and the crude product was chromatographed on silica gel to give the title compound (0.18 g) as colorless prisms from dichloromethanehexane. That the expected product was obtained was confirmed by the spectral data: MS: m/e 203 (M•+); NMR(CDCl$_3$): δ 1.54 (t, 3H, CH$_3$), 3.72 (s, 3H, CH—N), 4.24 (t, 2H, CH$_2$), 5.85 (s, 1H, CH=)

EXAMPLE 3

1-Benzyl-2-Methoxy-6-Methyl-4(1H)-Quinolinone (Compound No. 3 of Table I)

Ethereal diazomethane was added to a solution of the product of Preparation A (0.4 g) in dichloromethane (10 ml) containing methanol (1 ml), until a yellow color persisted and TLC showed the absence of starting material. The solution was evaporated to dryness and chromatographed on silica gel. The title compound was isolated as the minor product which was also more polar than the major product. Crystallization from ether-hexane gave prisms (70 mg). That the expected product was obtained was confirmed by the spectral data: MS: m/e 279 (M•+); NMR(CDCl$_3$): δ 240 (s, 3H, CH$_3$—Ar), 3.98 (s, 3H, OCH$_3$), 5.42 (s, 2H, CH$_2$—Ar), 5.82 (s, 1H, CH=), 8.22 (s, 1H, C$_5$—H).

EXAMPLE 4

1-Benzyl-2-Methoxy-4(1H)-Quinolinone (Compound No. 4 of Table I)

Prepared by starting with the product form Preparation B and following the procedure of Example 3. That the expected product was obtained was confirmed by the spectral data: MS: m/e 265 (M•+); NMR(CDCl$_3$): δ 1.72 (s, 3H, CH$_3$), 3.98 (s, 3H, OCH$_3$), 5.44 (s, 2H, CH$_2$), 5.98 (s, H, 3-H), 8.43 (dd, H, 5-H, J=12.3, 1).

EXAMPLE 5

1-Heptyl-2-Methoxy-4(1H)-Quinolinone (Compound No. 5 of Table I)

Prepared by starting with isatoic anhyride and following the procedures described for Preparation A and Example 3. That the expected product was obtained was confirmed by the spectral data: MS: m/e 273 (M•+); NMR(CDCl$_3$): δ 0.88 (t, 3H, CH$_3$), 1.29 (m, 8H(CH$_2$)$_4$), 3.95 (t, 2H, N—CH$_2$), 6.14 (s, H, 3-H), 8.02 (d, H5H, J=9), 12.73 (s, H, 4-OH).

EXAMPLE 6

1-Hexyl-2-Methoxy-8-Methyl-4(1H)-Quinolinone (Compound No. 6 of Table I)

Prepared by starting with 8-methylisatoic anhydride and following the procedures described for Preparation A and Example 3. That the expected product was obtained was confirmed by the spectral data: MS: m/e 273 (M•+); NMR(CDCl$_3$): δ 0.81 (s, 3H, CH$_3$), 2.60 (s, 3H, Ar—CH$_3$), 3.95 (s, 3H, CH$_3$O), 4.19 (t, 2H, N—CH$_2$CH$_2$), 5.84 (s, H, 3H), 8.23 (dd, H, 5H).

EXAMPLE 7

1-Hexyl-2,8-Dimethoxy-4(1H)-Quinolinone (Compound No. 7 of Table I)

Prepared by starting with 8-hydroxy-isatoic anhydride and following the procedures described for Preparation A and Example 3. That the expected product was obtained was confirmed by the spectral data: MS: m/e 289 (M•+); NMR(CDCl$_3$): δ 0.90 (t, 3H, CH$_3$) 1.30 (s, 6H, (CH$_2$)$_3$), 3.94 (s, 3H, CH$_3$O), 3.95 (s, 3H, CH$_3$O), 5.86 (s, H, 3H), 8.04 (dd, H, 5H).

EXAMPLE 8

1-[4-(t-Butyl-Dimethylsilyloxy)]Benzyl-2-Methoxy-6,7-Dimethyl-4-(1H)-Quinolinone (Compound No. 8 of Table I)

Prepared by starting with 6,7-dimethylisatoic anhydride and following the procedures described for Preparation A and Example 3. That the expected product was obtained was confirmed by the spectral data: MS: m/e 423 (M•+); NMR(CDCl$_3$): δ 0.175 (s, 6H, 2CH$_3$—Si), 0.954; 0.961 (s, 9H, SiC(CH$_3$)$_3$), 3.95 (s, 3H, OCH$_3$), 5.90 (s, H, 3-H), 8.15 (s, H, 5-H).

EXAMPLE 9

1-Benzyl-2-Methoxy-3-Carbethoxy-6-Methyl-4-(1H)-Quinolinone (Compound No. 9 of Table I)

Prepared from the product of Step (3) of Preparation A by following the procedure of Example 3. That the expected product was obtained was confirmed by the spectral data: MS: m/e 351 (M•+); NMR(CDCl$_3$): δ 1.42 (t, 3H, CH$_3$), 2.42 (s, 3H, CH$_3$—Ar), 4.00 (s, 3H, OCH$_3$), 4.47 (q, 2H, CH$_2$O), 5.48 (s, 2H, CH$_2$—Ar), 8.24 (s, 1H, C$_5$—H).

EXAMPLE 10

2,7-Dimethoxy-8-Methyl-1,4-Benzopyrone (Compound No. 10 of Table I)

Obtained by starting with 4,7-dihydroxy-8-methylcoumarin (JACS, 80, 140 (1958)) and following the procedure of Example 3. That the expected product was obtained was confirmed by the spectral data: MS: m/e 220 (M●⁻); NMR(CDCl₃): δ 2.22 (s, 3H, CH₃Ar), 3.88, 3.92 (ss, 6H, OCH₃), 5.50 (s, 1H, CH=), 7.98 (d, 1H, C₅—H).

Cell and Virus Culture

HeLa and Vero cell cultures were maintained in Eagles Minimal Essential Medium which was supplemented with glutamine, penecillin, streptomycin and 10% fetal calf serum (10% EMEM). Stock cultures of HSV-2 (strain MS available from ATCC VR-540) were grown in and harvested from Vero cells. Viral stocks were titered in Vero cells according to established procedures.

Plasmid Constructions

Plasmid pON 245$^{ori-}$ contains the promoter of the HSV-1 thymidine kinase (tk) gene located immediately 5' of the E. coli lac Z gene. In this arrangement, the tk promoter controls transcription from the bacterial gene in transient expression assays. Additionally, an SV40 polyadenylation signal is present at the 3' end of the lac Z gene to allow for the efficient translation of the mRNA in eucaryotic cells. The expression of beta galactosidase in a transient assay using pON 245$^{ori-}$ is dependent upon superinfection of the transfected cells with HSV. Therefore, a compound which interferes with early steps of HSV replication will also inhibit beta galactosidase production in transfected cells. For example, see U.S. application Ser. No. 07/435,491 filed Sep. 5, 1989, the disclosure of which is incorporated herein by reference thereto.

Transient Expression of Beta Galactosidase in Transfected Cells

HeLa cells were seeded into 96 well microtiter plates and allowed to grow to 80% confluency (approximately 35,000 cells/well). One half microgram of plasmid pON 245$^{ori-}$ DNA was introduced into the cells of each well by the DEAE Dextran precipitation technique (Graham and Van der Eb, 1973). Four to six hours later, the cells were rinsed with Hank's Balanced Salt Soluton (HBSS), overlaid with 10% EMEM and incubated at 37° C. At 24 hrs post-trasnfection, cells were rinsed, overlaid with 10% EMEM again and re-incubated at 37° C. At 48 hrs post-transfection, cells were rinsed and overlaid with either EMEM containing 2% fetal calf serum (2% EMEM, 2% EMEM containing HSV-2 (strain MS, Multiplicity of Infection [moi]=5 pfu/cell) or 2% EMEM containing the compound to be tested. Twenty-four hrs later, the cells were harvested and assayed to beta galactosidase activity as described below.

Beta Galactosidase Assay

All determinations of beta galactosidase activity were performed in 96 well microtiter plates. The intracellular level of beta galactosidase activity in each well was determined from cell lysates of the monolayer cultures. Aliquots were assayed by incubation in the presence of beta galactosidase substrate, 4-methylumbelliferyl-β-D-galactoside (MUG, 125 ug/ml, Sigma), for 2 hrs. The generation of fluorescent product was quantified on a Microfluor microfluorimeter (Dynatech) after addition of 0.1M glycine, pH 10.3 (Spaete and Mocarski, 1985). The inhibitory activity of a compound was plotted versus the concentration and an IC50 value (the concentration of compound required to reduce beta glactosidase expression by 50%) was obtained for each compound tested.

Compound Toxicity Assay

Compounds which demonstrated a significant inhibitory activity in the HeLa cell beta galactosidase assay were assayed for their inhibitory effect on HeLa cell translation. HeLa cells were treated with inhibitory compound for 24 hrs, after which levels of translational activity were assayed.

For assay of translational activity, HeLa cultures were grown to 80% confluency in 96 well microtiter plates, treated with appropriate concentrations of compound in 2% EMEM during an overnight incubation at 37° C., then rinsed with HBSS and overlaid with 0.8 ml of 2% EMEM containing 8 uCi of tritiated leucine ($^3$H-LEU, 141 Cu/mMol, Amersham Corp., Arlington Heights, Ill.). After a 1 hr incubation at 36.5° C., the cells were rinsed twice with phosphate buffered saline (PBS) and lysed in 400 ul/well of 1×PBS, 0.5% sodium dodecyl sulphate (SDS). After a 10 min incubation at 36.5° C., the contents of the well were transferred to a well in a Millititer HA microfiltration plate (Millipore Corp., Bedford, Mass.). The TCA insoluble proteins were precipitated onto the filter disc by a 10 min fixation with 5% TCA, followed by filtration over vacuum and three 10 minute rinses with 95% ethanol. The filters were dried at room temperature, cut from the milltitier plate and transferred to scintillation vials. TCA precipitable counts were assayed in 5 ml of Scintisol (Isolab, Akron, Ohio). The inhibitory activity of a compound was plotted versus the concentration and an IC50 value (that concentration of the compound required to decrease cellular translational activity by 50%) was derived for each compound.

In-Vitro Anti-HSV Activity

The in-vitro anti-HSV activity of compounds of this invention is set forth in Table II.

TABLE II

| Compound No. (Table I) | Anti-HSV Activity HSV-β-Gal Assay IC₅₀ (μg/ml) | Cytotoxicity $^3$H-LEU Assay IC₅₀ (μg/ml) |
| --- | --- | --- |
| 1 | >25 | — |
| 3 | 13 | 85 |
| 4 | 20 | 45 |
| 5 | 9 | 45 |
| 6 | 3.6* | 27 |
| 7 | 5.8* | 21 |
| 8 | 2 | 25 |
| 9 | 3 | 79 |
| 10 | 18 | >100 |
| 11 | 10 | — |
| 12 | 4 | 12 |
| 13 | 4 | 27 |
| 14 | >25 | — |

*Repeat

ANTIHYPERTENSIVE ACTIVITY

I. SHR Analysis

The ability of the antihypertensive compounds of the present invention to lower blood pressure can be assessed in vivo in conscious spontaneously hypertensive rats (SHR). SHR males are purchased from Taconic Farms, Germantown, N.Y. and are approximately 16–18 weeks old when anesthetized with ether. The caudal (ventral tail) artery is cannulated with polyethylene tubing (PE50) and blood pressure and heart rate are recorded as described by Baum. T. et al. J. Cardiovasc. Pharmacol. Vol. 5, pp. 665–667, (1983). Rats are placed into plastic cylindrical cages where they rapidly recover consciousness. Blood pressure and heart rate are allowed to stabilize for approximately 90 minutes prior to compound administration. Compounds are administered orally as solutions or suspensions in 0.4% aqueous methylcellulose vehicle via a feeding needle. The compound or 0.4% aqueous methylcellulose vehicle are given in a volume of 4 ml/kg to SHRs that had been fasted overnight. Activity is expressed as the fall in mean blood pressure (MBP) in millimeters of mercury (mm Hg). Compound-induced changes are compared with the changes in an appropriate placebo group.

The SHR results are set forth in Table III.

II. Phosphodiesterase Inhibition in vitro

The antihypertensive compounds of this invention are useful in inhibiting the phosphodiesterase enzyme. These phosphodiesterase enzymes are known to hydrolyze cGMP in smooth muscle. High levels of cGMP are associated with the relaxation of vascular smooth muscle, with a consequence subsequent reduction blood pressure. Thus, it is believed that by inhibiting these phosphodiesterase enzymes, cGMP levels in muscle will be either maintained or increased with a subsequent reduction in blood pressure.

Compounds are evaluated for inhibition of a phosphodiesterase enzyme which hydrolyzes cyclic guanosine monophosphate (cGMP). The enzyme, cGMP phosphodiesterase (cGMP-PDE), is a homogeneous enzyme obtained from bovine lung and purified by ion-exchange chromatography, gel filtration, and sucrose gradient centrifugation. cGMP-PDE is highly selective for cGMP. Bovine aorta homogenates and primary cultures of bovine aortic endothelial and vascular smooth muscle cells contain an enzyme with properties very similar to the lung isozyme.

The enzyme assay is performed using a Biomek Automated Pipetting Station. Compounds are dissolved in distilled water or DMSO and diluted with 10% DMSO. Compounds are tested at several concentrations at log intervals, typically 0.1, 1.0, 10, and 100 μM final concentration.

Assays contain the following components:
1 μM substrate $^3$H-cGMP
50 mM Tris-HCl, pH 7.5, 5 mM magnesium chloride (MgCl$_2$)
0.5 mg/ml snake venom alkaline phosphatase Assays are initiated by addition of enzyme and stopped by addition of 10 mM isobutylmethylxanthine, a general phosphodiesterase inhibitor. Assays are performed for 25 minutes at room temperature to achieve 5–10% hydrolysis of substrate. The negatively charged substrates are then separated from guanosine by binding to an anion-exchange resin (AGI-X8) and centrifugation or filtration, and the product is quantitated by scintillation counting in counts.

% Inhibition = 100 − [(cpm compound-blank)/(cpm control-blank) × 100]

Activity is expressed as the IC$_{50}$ value, i.e., the concentration required to inhibit activity of the enzyme by 50 percent. The cGMP-PDE IC$_{50}$ results are set forth in Table III.

TABLE III

ANTIHYPERTENSION RESULTS

| Compound No. (Table 1) | cGMP-PDE IC$_{50}$ (μM) | SHR Dosage (mpk)[1] | MBP (mm of Hg) |
|---|---|---|---|
| 3 | 6 | — | — |
| 4 | 2.6 | — | — |
| 5 | 5.9 | — | — |
| 10 | 13.0 | — | — |
| 15 | — | 25(P.O.) | 12 |
| 16 | 0.6 | — | — |
| 17 | 14.0 | — | — |

[1] mpk: mg per kg of body weight

Compounds within the scope of the antihypertensive compounds of this invention which did not give optimum antihypertensive activity with the SHR and/or phosphodiesterase assays used above are listed in Table IV. In Table IV Ph represents phenyl.

TABLE IV

| R | R$_1$ | R$_2$ | R$_3$ | cGMP-PDE IC$_{50}$ (μM) | SHR MBP (mm of Hg) |
|---|---|---|---|---|---|
| H | —CH$_3$ | 6-OCH$_2$Ph | —CH$_2$Ph | >100 | — |
| H | —CH$_3$ | 6-OCH$_3$ | —CH$_2$Ph | >100 | — |
| H | —CH$_3$ | — | —CH$_2$CO$_2$CH$_3$ | >100 | — |
| H | —CH$_3$ | 7-Cl | —CH$_3$ | >100 | −7[1] |
| H | —CH$_3$ | 8-CH$_3$ | C$_6$H$_{13}$ | >100 | −1[1] |

[1] at 25 mpk (p.o.)

The invention being thus described, it will be obvious that the same may be varied in many ways. Such variations are not to be regarded as a departure from the spirit and scope of the invention and all such modifications are intended to be included within the scope of the claims.

What is claimed is:

1. A compound of Formula 1.0

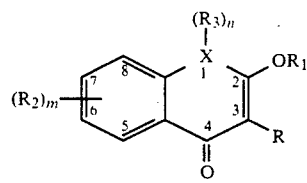

(A) R is selected from H, Cl, I and —C(O)OC$_2$H$_5$;
(B) R$_1$ is methyl;
(C) R$_2$ is selected from the group consisting of: methyl and methoxy; and
(D) R$_3$ is selected from the group consisting of: hexyl, heptyl, benzyl, 4-hydroxybenzyl, and 4-t-butyldimethylsilyloxybenzyl.

2. A compound of claim 1
(A) R is selected from the group consisting of: H and —C(O)C$_2$H$_5$; and
(D) R$_3$ is selected from the group consisting of hexyl, heptyl and benzyl.

3. The compound of claim 1 wherein said compound is selected from the group consisting of:

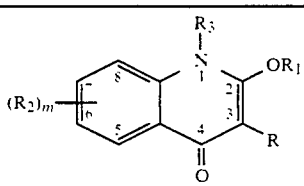

| No. | R | $R_1$ | $R_2$ | $R_3$ |
|---|---|---|---|---|
| 3 | H | —$CH_3$ | 6-$CH_3$ | Bzl |
| 4 | H | —$CH_3$ | — | Bzl |
| 5 | H | —$CH_3$ | — | —$C_7H_{15}$ |
| 6 | H | —$CH_3$ | 8-$CH_3$ | —$C_6H_{13}$ |
| 7 | H | —$CH_3$ | 8-$OCH_3$ | —$C_6H_{13}$ |
| 8 | H | —$CH_3$ | 6-$CH_3$ 7-$CH_3$ | SiOBzl |
| 9 | —$C(O)OCH_2H_5$ | —$CH_3$ | 6-$CH_3$ | Bzl |
| 10 | H | —$CH_3$ | 7-$OCH_3$ 8-$CH_3$ | — |
| 11 | H | —$CH_3$ | 6-$CH_3$ 7-$CH_3$ | 4-OHBzl |
| 12 | Cl | —$CH_3$ | 6-$CH_3$ | Bzl |
| 13 | I | —$CH_3$ | — | Bzl |
| 16 and | H | —$CH_3$ | 6-$CH_3$ | —$C_6H_{13}$ |
| 17 | —$C(O)OC_2H_5$ | —$CH_3$ | — | —$C_6H_{13}$ | wherein:
(1) SiOBzl represents 4-t-butyldimethylsilyloxybenzyl:

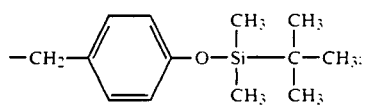

(2) SiOBzl represents 4-hydroxybenzyl:

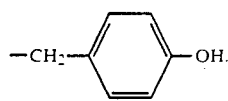

4. A compound of claim 3 wherein said compound is selected from the group consisting of compounds represented by compound numbers 3,4,5,6,7,8,9,10,11,12, and 13 of Table I.

5. A pharmaceutical composition comprising an effective amount of a pharmaceutically acceptable carrier and an antivirally or antihypertensively effective amount of a compound of claim 1.

6. A pharmaceutical composition comprising an effective amount of a pharmaceutically acceptable carrier and an antivirally or antihypertensively effective amount of a compound of claim 2.

7. A method of treating a hypertension in a patient in need of such treatment comprising administering an effective amount of a compound of claim 1 to said patient.

8. A method for treating hypertension in a patient in need of such treatment comprising administering an effective amount of a compound selected from the group consisting of:

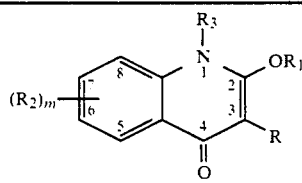

| No. | R | $R_1$ | $R_2$ | $R_3$ |
|---|---|---|---|---|
| 3 | H | —$CH_3$ | 6-$CH_3$ | Bzl |
| 4 | H | —$CH_3$ | — | Bzl |
| 5 | H | —$CH_3$ | — | —$C_7H_{15}$ |
| 6 | H | —$CH_3$ | 8-$CH_3$ | —$C_6H_{13}$ |
| 7 | H | —$CH_3$ | 8-$OCH_3$ | —$C_6H_{13}$ |
| 8 | H | —$CH_3$ | 6-$CH_3$ 7-$CH_3$ | SiOBzl |
| 9 | —$C(O)OCH_2H_5$ | —$CH_3$ | 6-$CH_3$ | Bzl |
| 10 | H | —$CH_3$ | 7-$OCH_3$ 8-$CH_3$ | — |
| 11 | H | —$CH_3$ | 6-$CH_3$ 7-$CH_3$ | 4-OHBzl |
| 12 | Cl | —$CH_3$ | 6-$CH_3$ | Bzl |
| 13 | I | —$CH_3$ | — | Bzl |
| 16 and | H | —$CH_3$ | 6-$CH_3$ | —$C_6H_{13}$ |
| 17 | —$C(O)OC_2H_5$ | —$CH_3$ | — | —$C_6H_{13}$ |

* * * * *

UNITED STATES PATENT AND TRADEMARK OFFICE
CERTIFICATE OF CORRECTION

PATENT NO. : 5,175,151
DATED : December 29, 1992
INVENTOR(S) : Adriano Afonso; Jay Weinstein, Margaret J. Gentles It is certified that error appears in the above-identified patent and that said Letters Patent is hereby corrected as shown below:

In column 22, line 42 which is claim 1, line 1 delete "Formula 1.0" and insert therefor -- the formula --.

In column 22, line 43 which is claim 1, line 2

(( ))

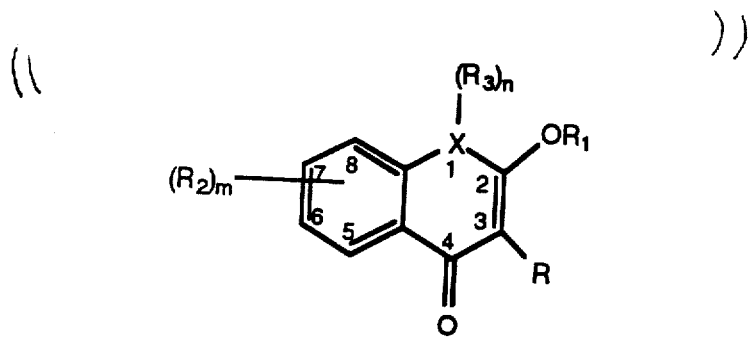

UNITED STATES PATENT AND TRADEMARK OFFICE
CERTIFICATE OF CORRECTION

PATENT NO. : 5,175,151
DATED : December 29, 1992
INVENTOR(S) : Adriano Afonso; Jay Weinstein, Margaret J. Gentles It is certified that error appears in the above-identified patent and that said Letters Patent is hereby corrected as shown below:

should read

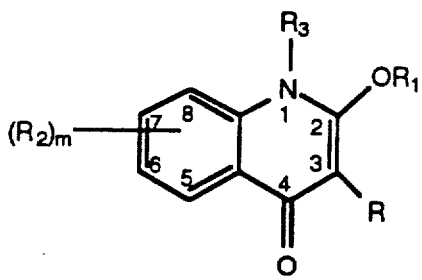

Right after column 22, line 43 which is right after claim 1, line 2 insert -- wherein --.

In column 22, line 61 which is claim 2, line 1 after the word "claim 1" insert -- wherein --.

Signed and Sealed this

Twenty-fifth Day of January, 1994

Attest:

BRUCE LEHMAN

*Attesting Officer*    Commissioner of Patents and Trademarks